United States Patent [19]

Perka et al.

[11] Patent Number: 4,946,477

[45] Date of Patent: Aug. 7, 1990

[54] IGCC PROCESS WITH COMBINED METHANOL SYNTHESIS/WATER GAS SHIFT FOR METHANOL AND ELECTRICAL POWER PRODUCTION

[75] Inventors: Alan T. Perka, Macungie; Thomas H. Hsiung, Emmaus; Joseph Klosek, Wescosville; Robert B. Moore, Allentown, all of Pa.

[73] Assignee: Air Products & Chemicals, Inc., Allentown, Pa.

[21] Appl. No.: 178,955

[22] Filed: Apr. 7, 1988

[51] Int. Cl.$^5$ ............................................. C07C 31/04
[52] U.S. Cl. ................................. 48/197 R; 518/700; 518/708; 518/711
[58] Field of Search ................ 518/700, 711, 703–705, 518/706, 708; 48/197 R, 202, 206, 211, 215, DIG. 7; 252/373

[56] References Cited

U.S. PATENT DOCUMENTS 2,665,289  1/1954  Arnold ................................. 518/711
4,477,594  10/1984  Greene et al. ....................... 518/700

FOREIGN PATENT DOCUMENTS 59-207827  11/1984  Japan ..................................... 55/16

OTHER PUBLICATIONS

Sherwin et al., "Liquid-Phase Methanol", EPRI Report AF-1291, pp. 5/3–5/7, Dec. 1979.
Vedage et al., "Water Promotion and Identification of Intermediates in Methanol Synthesis", Proceedings, 8th International Congress on Catalysis, vol. II, pp. 47–58, 1984.

Primary Examiner—Joye L. Woodard
Attorney, Agent, or Firm—John M. Fernbacher; James C. Simmons; William F. Marsh

[57] ABSTRACT

The present invention relates to an improvement to a process for the production of methanol from synthesis gas containing carbon monoxide and hydrogen utilizing a three phase or liquid-phase reaction technology. The improvement to the process is the addition of relatively small amounts of water to the liquid-phase reactor thereby allowing for the use of a CO-rich synthesis gas for the production of methanol by effectuating in the same reactor the methanol synthesis and water-gas shift reactions. A portion of the unreacted synthesis gas stream from the liquid-phase reactor is separated into a hydrogen-rich component and a carbon monoxide-rich component. The hydrogen-rich component is combined with a portion of the unreacted synthesis gas stream from the liquid-phase reactor to form a gas-phase methanol reactor feed stream for producing methanol, and the carbon monoxide-rich component is combined with the unreacted effluent from the gas-phase methanol reactor to form a feed stream for combustion in a gas turbine.

3 Claims, 10 Drawing Sheets

IGCC PROCESS WITH COMBINED METHANOL SYNTHESIS/WATER GAS SHIFT FOR METHANOL AND ELECTRICAL POWER PRODUCTION

TECHNICAL FIELD

The present invention relates to an integrated gasification combined cycle (IGCC) process. More specifically, the present invention relates to an improvement which converts a portion of the produced, CO-rich synthesis gas to produce a crude methanol product for peak-shaving.

BACKGROUND OF THE INVENTION

Methanol is produced from synthesis gas (syngas), a mixture of hydrogen ($H_2$). carbon monoxide (CO), and carbon dioxide ($CO_2$). The stoichiometry of the methanol synthesis reactions indicates that the desired molar reactor feed composition is given by the equation:

$$R = (H_2 - CO_2)/(CO + CO_2) = 2.0$$

However, reaction kinetics and system control dictate that the optimum ratio is actually $R = 2.1$ or higher. Gas with $R = 2.0$ to 2.1 is called "balanced" gas, i.e. balanced stoichiometrically, and has a typical composition of 19% CO, 5% $CO_2$, 55% $H_2$, and 21% $CH_4$—$N_2$.

Syngas is commonly made by the reforming of methane or other hydrocarbons, which gives a hydrogen-rich gas well-suited for methanol synthesis (e.g., a typical methanol syngas produced by steam reforming of methane has a composition of 15% CO, 8% $CO_2$, 73% $H_2$, 4% $CH_4$—$N_2$, $R = 2.8$). Currently 70 to 75% of the world's methanol comes from reformed natural gas, however, because of the instability of the oil market, liquid hydrocarbons and natural gas are not always readily available or available at an inexpensive cost. An alternative and abundant resource is coal, which can be converted to syngas in a coal gasifier such as the advanced, high-temperature coal gasifiers developed by Texaco, Dow, Shell, and British Gas/Lurgi.

Coal-derived syngas can be used as gas turbine fuel in an integrated gasification combined cycle (IGCC) electric power plant. Because of the daily cyclical demand for power, a primary concern in such a facility is load-following flexibility. To accomplish this flexibility, either the front end of the IGCC plant must be built for peak capacity, or extra fuel must be imported during peak periods (called peak shaving). The former is an expensive and inefficient option. The latter, although somewhat less expensive, can be improved by producing and storing the fuel on-site. One solution to this problem is the on-site production of methanol as the peak-shaving fuel.

In an IGCC facility without methanol coproduction, the syngas is combusted in a gas turbine to produce electricity. The turbine exhaust/stack gas is used to generate and superheat steam in an integrated heat recovery system, and this steam is also used to generate electricity. In a coproduction facility, the syngas is first passed through a methanol synthesis reactor to convert a portion to methanol; the remaining syngas is fed to the gas turbine for power production. The methanol is stored as peak-shaving fuel, which is used to augment the feed to the gas turbine during periods of high power demand. This scheme is attractive because the load on a power plant varies over a wide range, and it is more economical to feed the stored methanol than to build peak-shaving capacity into the front end of the facility.

Unfortunately, coal-derived syngas from advanced gasifiers used in IGCC plants is CO-rich (e.g., a Texaco gasifier syngas has a typical composition of 35% $H_2$, 51% CO, 13% $CO_2$, 1% $CH_4$—$N_2$; $R = 0.34$), unlike the hydrogen-rich syngas from reformed hydrocarbons. The problem is that converting this gas to methanol by conventional methods is expensive and complicated because several pretreatment steps are required to balance the gas prior to methanol synthesis.

Conceptual IGCC coproduct plants have been designed with gas-phase and with liquid-phase methanol synthesis reactors. With a gas-phase reactor, the main syngas stream from the gasifier is divided into two parts: approximately 75% goes directly to the gas turbine, and the remaining 25% goes to the methanol synthesis section. This latter stream is further divided, approximately 67% being mixed with steam and sent to a high temperature shift reactor (HTS). After shift, the $CO_2$ is removed and this stream is remixed with the unshifted stream and recycle gas in the methanol loop to give a balanced gas for methanol synthesis. Purge gas from the recycle loop and the rejected $CO_2$ from the $CO_2$ removal section are sent to the gas turbine. The use of a conventional, gas-phase methanol synthesis reactor in an IGCC coproduct scheme is subject to the same shortcomings as in a gas-phase all-methanol product plant: a shift section and $CO_2$ removal section are required in order to achieve a feed gas composition with an "R" value greater than 2.0, shift and methanol synthesis are performed in separate vessels, and the conversion per pass is limited by temperature constraints.

The liquid-phase methanol process has an advantage over gas-phase methanol synthesis in a coproduct configuration because of its ability to directly process CO-rich gas (e.g., "R" values between about 0.30 and 0.40). The entire CO-rich gas stream from the gasifier is sent through the liquid-phase reactor in a single pass, achieving 10–20% conversion of CO to methanol. While additional methanol can be produced by balancing the gas prior to feeding it to the liquid-phase methanol reactor, the value of this incremental methanol is outweighed by the cost of separate shift and $CO_2$ removal units. Because a liquid-phase methanol reactor operates isothermally, there is no increasing catalyst temperature and the accompanying constraint on methanol conversion which is characteristic of gas-phase methanol synthesis processes. In a typical liquid-phase design, approximately 14% of the CO (feedgas "R" = 0.34) is converted to methanol, giving a reactor effluent containing approximately 9% methanol; the per pass conversion in a gas-phase reactor generally results in a reactor effluent containing only 5% methanol even though the feedgas has an "R" greater than 2.0. It should be noted, however, that even with the superior performance of the liquid-phase reactor, the coproduction scheme can still be expensive, and there is incentive to improve this processing route.

A somewhat similar coproduction scheme is also worthy of mention (U.S. Pat. No. 3,986,349 and 4,092,825). This scheme involves converting coal-derived syngas into liquid hydrocarbons via Fischer-Tropsch synthesis, separating the hydrocarbons from the unreacted gas, feeding the gas to a gas turbine to generate electric power, and using at least part of the hydrocarbons as peak-shaving fuel. Although methanol is mentioned as a possible by-product of the hydrocarbon synthesis, it is not one of the desired products.

SUMMARY OF THE INVENTION

The present invention is an improvement to an integrated gasification combined cycle (IGCC) electric power plant process. The IGCC process converts hydrocarbon fuels in a gasifier producing a CO-rich synthesis gas, which in turn is combusted in a gas turbine to produce power. The IGCC process also includes a provision for production of methanol from the CO-rich synthesis gas prior to combustion as a supplemental fuel, which can be used to peak-shave. Methanol is produced by reacting at least a portion of the CO-rich synthesis gas in the presence of a methanol synthesis catalyst.

The improvement for increasing methanol productivity from the same amount of synthesis gas is the combination of the water/gas shift and methanol synthesis reactions in a single step by reacting the carbon monoxide-rich synthesis gas with water in the presence of a catalyst in a liquid-phase reactor thereby producing both a crude methanol product and a reduced carbon monoxide content and increased hydrogen and carbon dioxide content synthesis gas. The produced reduced carbon monoxide content and increased hydrogen and carbon dioxide content synthesis gas is suitable for combustion in a gas turbine.

The water added to the liquid-phase reactor can be beneficially introduced as a liquid. The catalyst in the liquid-phase reactor can be any appropriate methanol synthesis catalyst or a mixture of a methanol synthesis catalyst and a low temperature shift catalyst. The catalyst concentration in the liquid-phase methanol reactor can be in the range from about 5 to about 50 weight percent. The improvement to the process of the present invention is particularly suited to CO-rich synthesis gases having an R value less than 2.0.

The present invention also comprises several further processing steps. Among these are (1) processing at least a portion of the reduced carbon monoxide and increased hydrogen and carbon dioxide synthesis gas in, for example, a membrane unit or a pressure swing adsorber (PSA) unit to separate the reduced carbon monoxide and increased hydrogen and carbon dioxide synthesis gas into a hydrogen-rich component and a carbon monoxide-rich component, both components comprising hydrogen, carbon dioxide and carbon monoxide, and recycling the hydrogen rich component to the inlet of the liquid-phase reactor; and (2) processing at least a portion of the reduced carbon monoxide and increased hydrogen and carbon dioxide synthesis gas in, for example, a membrane unit or a pressure swing adsorber (PSA) unit to separate the reduced carbon monoxide and increased hydrogen and carbon dioxide synthesis gas into a hydrogen-rich component and a carbon monoxide-rich component, both components comprising hydrogen, carbon dioxide and carbon monoxide, combining the hydrogen-rich component and a portion of the unprocessed synthesis gas (i.e., the gas not processed in the membrane or PSA units) into a single methanol reactor feed stream, optionally removing at least a portion of the carbon dioxide from the gas-phase methanol reactor feed stream, reacting the methanol reactor feed stream in a gas-phase reactor to produce methanol, and combining the unconverted effluent from the gas-phase methanol reactor with the carbon monoxide-rich component from the membrane unit to form a gas turbine combustion feed.

BRIEF DESCRIPTION OF THE DRAWING

FIG. 5 shows the process without water addition and FIG. 6 with water addition.

FIG. 7 shows the process without water addition and FIG. 8 with water addition.

FIG. 9 shows the process without water addition and FIG. 10 with water addition.

DETAILED DESCRIPTION OF THE INVENTION

The present invention is an improvement to the methanol production step within an integrated gasification combined cycle process wherein methanol is produced for peak-shaving from CO-rich synthesis gas. The improvement to the process is the combination of the methanol synthesis and water-gas shift reactions in a single step in order to increase methanol productivity. The improvement of the present invention replaces the need to balance the synthesis gas in shift and $CO_2$ removal steps prior to its conversion to methanol as would be required if a gas-phase methanol synthesis process were used. The present invention is based on the fact that if water is added to the CO-rich syngas feed to a liquid-phase methanol reactor, the water-gas shift and methanol synthesis reactions will take place simultaneously. In fact, if no water is added the reverse water-gas shift reaction is known to take place in either liquid or gas-phase reactors. The addition of water simply forces the equilibrium in the forward direction (i.e., $CO + H_2O \rightarrow H_2 + CO_2$).

Several advantages of the liquid-phase methanol reactor have already been mentioned. An additional advantage is seen when considering water addition. In contrast to conventional technologies, liquid water can be added directly to the liquid-phase reactor. This saves the cost of generating high-pressure process steam, and also reduces the net heat which must be removed from the reactor. A conventional gas-phase reactor cannot accept a liquid water feed because thermal shock and rapid vaporization can break up and destroy the catalyst tablets. In addition, water vapor which is added must be kept well above its dew point to prevent condensation and subsequent quenching of the bed due to its plug flow operation.

Although the addition of steam to a liquid-phase methanol reactor was considered in EPRI Report AF-1291 (December 1979, p. 5-3), wherein the concept is discussed, and laboratory data is presented for two syngas compositions, the data indicated that methanol productivity decreases as water is added. It was reported that water addition always reduces methanol productivity, especially for gases that already have the required $H_2/CO$ stoichiometry, and that for non-stoichiometric synthesis gases, the fall off in productivity with increasing steam/CO ratio is slower.

Figure 1:
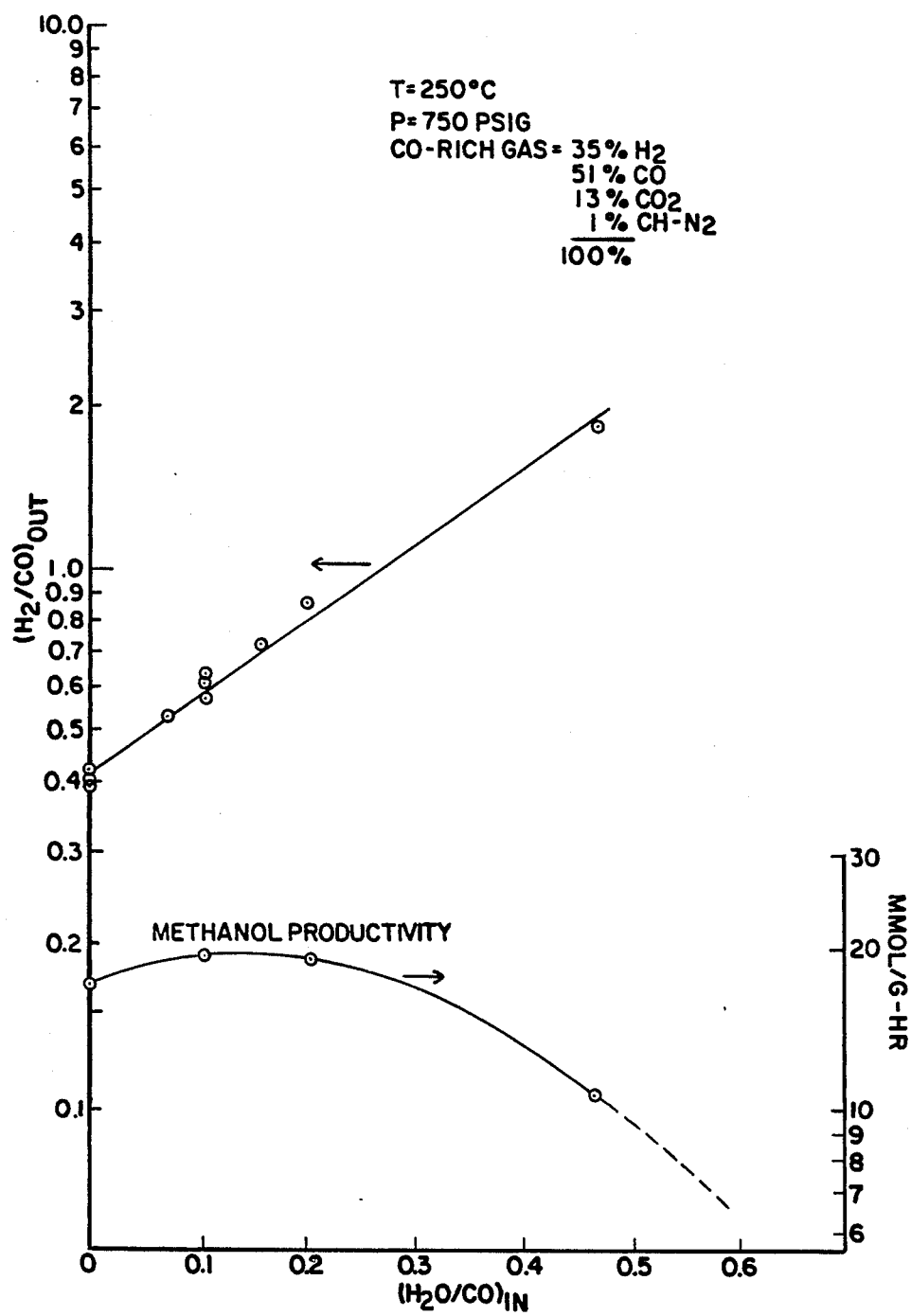
FIG. 1 is a plot showing the effect of water, expressed as molar $H_2O/CO$ ratio entering the liquid-phase methanol reactor, on methanol productivity and on the hydrogen content leaving the liquid-phase methanol reactor.

The experimentation behind the present invention, on the other hand, shows results which are surprising relative to those in the EPRI report. FIG. 1 shows the effect of water, expressed as the molar $H_2O/CO$ ratio entering the liquid-phase methanol reactor, on methanol productivity (mmol MeOH/hr-gm catalyst) and on the molar $H_2/CO$ ratio (a measurement of the extent of the water-gas shift reaction) leaving the liquid-phase methanol reactor. This graph illustrates two important points. First, the methanol productivity curve goes through a maximum, showing that water indeed can be used to boost methanol productivity. This maximum was not seen or even suspected in the data reported in EPRI Report AF-1291. Second, adding water increases the hydrogen content in the effluent. Although the $CO_2$ produced from the shift reaction prevents a stoichiometrically balanced effluent, the proper amount of $CO_2$ can be removed later to give a balanced gas, if desired. Thus, adding a precise amount of water results in increased methanol production relative to dry CO-rich gas feed as well as a notable production of $H_2$ via the shift reaction. Adding more water results in increased $H_2$ production at some sacrifice to methanol productivity.

Figure 2:
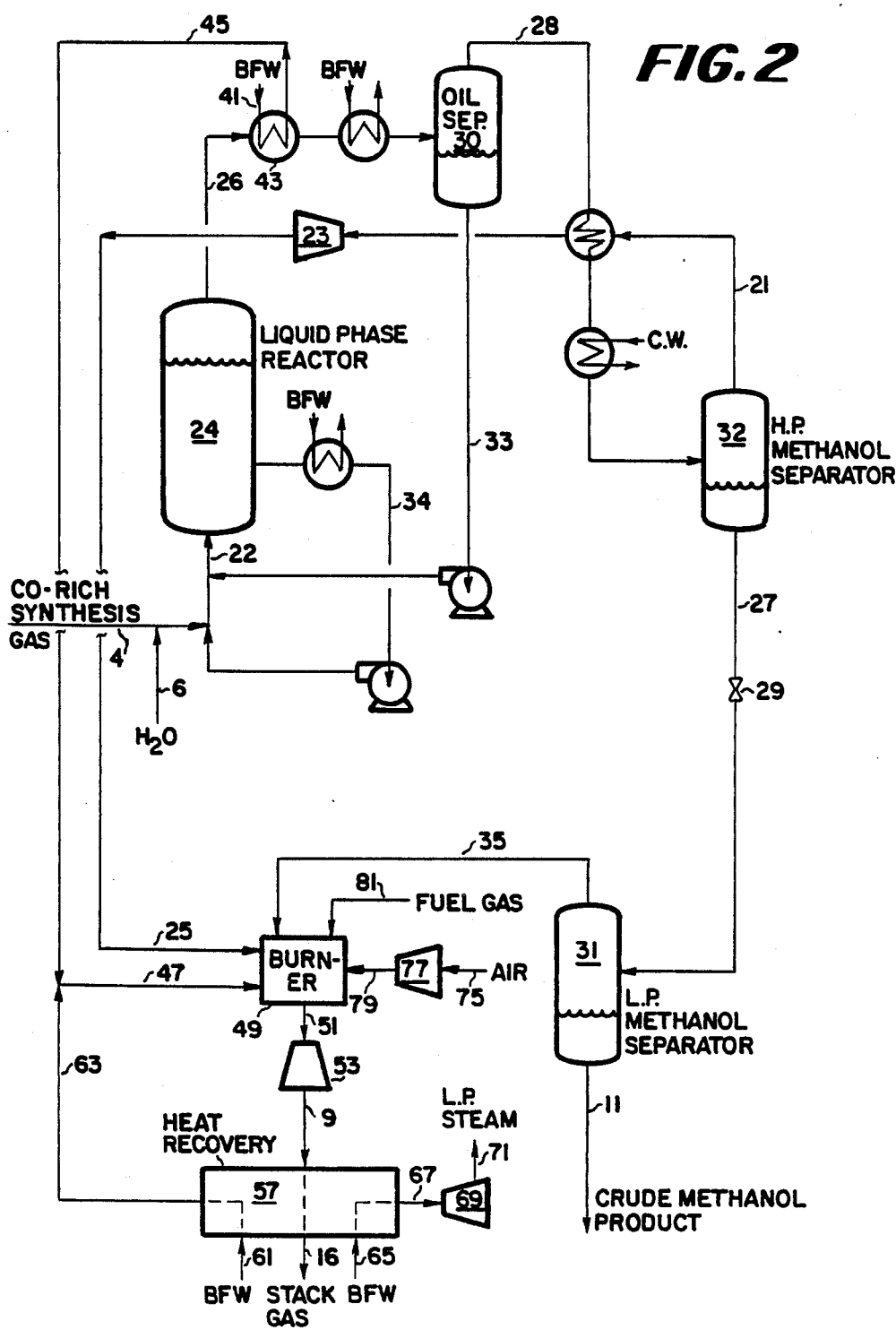
FIG. 2 is a schematic diagram of an embodiment of the methanol synthesis and combustion turbine sections of an IGCC power plant according to the present invention.

The proposed IGCC coproduct plant flowsheet according to the present invention is shown in FIG. 2. With reference to FIG. 2, desulfurized CO-rich synthesis gas and water (liquid or vapor) are fed to the process via lines 4 and 6, respectively, combined, and fed to liquid-phase reactor 24 via line 22, wherein the synthesis gas and water react in the presence of a catalyst. Alternatively, the liquid water or steam, in line 6, can be added directly to reactor 24 without first being combined with the synthesis gas. Liquid-phase methanol reactor 24 can be operated in either a slurry or ebullated mode. In the case of the slurry mode, a powdered methanol synthesis catalyst (e.g., $CuO/ZnO/Al_2O_3$) is slurried in a liquid medium (e.g light paraffinic or cycloparaffinic oils). Alternatively, a mixture of powdered methanol synthesis catalyst and low temperature shift catalyst can be used in reactor 24. The concentration of catalyst can range from about 5 to 50 wt %. In the case of an ebullated mode, a granulated catalyst is fluidized in a liquid medium. Liquid-phase reactor 24 operates within the conventional understanding of a liquid-phase reactor.

The effluent removed via line 26 from liquid-phase reactor 24 is cooled in a series of heat exchangers, including heat exchanger 43, and subsequently separated in separator 30 into a liquid and vapor stream. The primary purpose of separator 30 is to recover and recycle the liquid medium which was vaporized and entrained in the reactor effluent. The liquid stream is recycled via line 33 to liquid-phase reactor 24. Additionally, to provide heat removal from reactor 24, a liquid stream is removed from the reactor via line 34, cooled and returned to reactor 24.

The vapor stream from oil separator 30 is removed via line 28, cooled in a series of heat exchangers so as to condense methanol and water in the stream and then fed to high pressure methanol separator 32. The overhead from separator 32 is removed via line 21; this overhead is mainly unreacted synthesis gas, which is then reduced in pressure in expander 23 to recover power and subsequently fed to burner 49 via line 25.

The liquid phase from separator 32 is removed via line 27, reduced in pressure in J-T valve 29 and fed to low pressure methanol separator 31. In separator 31, dissolved synthesis gas in the methanol and water solution is removed as overhead via line 35 and fed as feed to burner 49. The bottoms of separator 31 is removed via line 11 as crude methanol product.

The above is a description of a once through methanol synthesis portion of an IGCC process. The combustion portion of the IGCC cycle is as follows: As mentioned earlier, the unreacted synthesis gas from the methanol synthesis portion is fed to burner 49 via lines 25 and 35. These streams are combusted in burner 49 along with fuel gas produced from the sulfur removal step of the gasifier portion of an IGCC facility (fed via line 81), compressed air and steam. The compressed air is introduced to the process via line 75, compressed in compressor 77 and introduced into the burner via line 79. Steam is produced and introduced into the burner through two heat sources. First, boiler feed water, in line 41, is heated in heat exchanger 43 against the effluent, line 26, from liquid-phase reactor 24 producing steam in line 45. Second, boiler feed water, in line 61, is heated in heat recovery unit 57 producing steam in line 63. These two steam streams, lines 45 and 63 are combined into stream 47 which is then fed to burner 49.

The combustion gas from burner 49 is fed to gas turbine expander 53 via line 51 for recovery of power and subsequently fed to heat recovery unit 57 via line 9. In heat recovery unit 57, energy is recovered from the expanded combustion gas by producing steam and superheating steam by heat exchange of the combustion gas with boiler feed water and saturated steam. A portion of the steam produced in heat recovery unit 57 is introduced as feed to burner 49. The remaining portion of steam, in line 67, which is produced from boiler feed water introduced via line 65, is expanded in turbine 69 producing both power and low pressure steam.

In the above description, stream 4 represents desulfurized CO-rich gas from a Texaco coal gasifier; stream 6 can be used to supply water such that the combined streams (line 22) have a molar ratio of $H_2O/CO=0.17$. As shown in FIG. 1, this is approximately the ratio necessary to achieve the maximum methanol production. Stream 22 is fed to liquid-phase reactor 24, which typically operates at about 482° F. and 910 psia. Reaction heat is removed in an external heat exchange loop which produces saturated steam. The reactor effluent is cooled by first producing steam, then by heat exchange with unreacted fuel gas, and finally with cooling water. The two-phase mixture is separated and the vapor is heated and expanded, producing electric power. This expanded fuel gas is then sent to the gas turbine burner. The condensed methanol is flashed to yield the crude methanol product and a residual gas stream which is also fed to the gas turbine burner. In addition to the main fuel gas and flash gas streams, the gas turbine burner also receives a fuel gas stream from the upstream sulfur removal plant (e.g., Selexol, Rectisol, Rectisol II), sufficient steam from the process to control $NO_x$ production, and compressed air. These streams are fed to the combustion zone, which typically operates at 2000° F. The burner effluent expands across the gas turbine expander, which produces electric power for export and for running the air compressor. The gas turbine exhaust is used to produce and superheat steam in an integrated heat recovery system. The steam subsequently powers steam turbines which produce additional electric power.

An IGCC coproduct plant without water addition has two principal modes of operation. During peak power demand times, all of the fuel gas and some stored methanol go to the gas turbine. During off-peak hours, gas flows through the liquid-phase reactor to convert a portion of the gas to methanol for storage. With water addition, the methanol productivity per mass of catalyst is increased, which means that either the reactor can be downsized or additional methanol can be produced from a base-size unit. The plant has greater flexibility because it can operate in three modes: all fuel gas to the gas turbine, gas through the liquid-phase reactor without water addition, and gas through liquid-phase reactor with water added.

Figure 3:
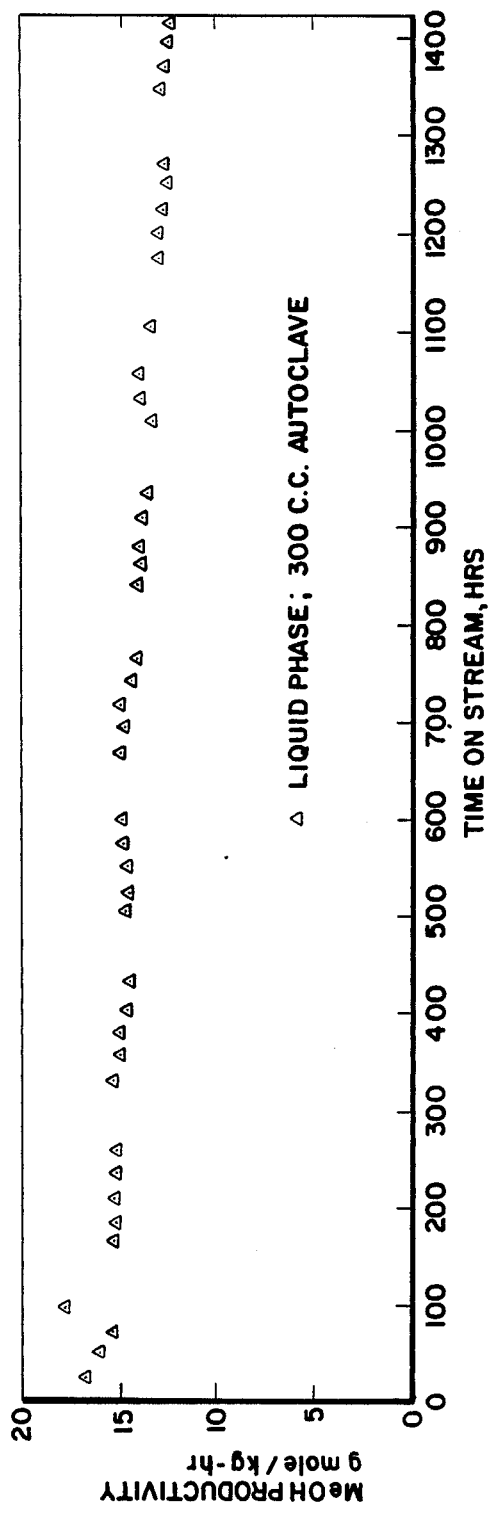
FIG. 3 is a plot of methanol productivity for a typical liquid-phase run without water addition.

An additional, surprising benefit of water addition has been demonstrated in the laboratory. FIG. 3 shows methanol productivity for a typical liquid-phase run with balanced syngas without water addition. Productivity falls off with time onstream from around 17 to 12.5 gmole/hr-kg. FIG. 3 illustrates the expected and well-known fact that methanol synthesis catalyst deactivates with time. FIG. 3 also illustrates a characteristic of methanol synthesis catalyst life curves, in that there is an early period of hyperactivity during which the catalyst deactivates sharply; after this hyperactivity period the catalyst deactivates slowly.

Figure 4:
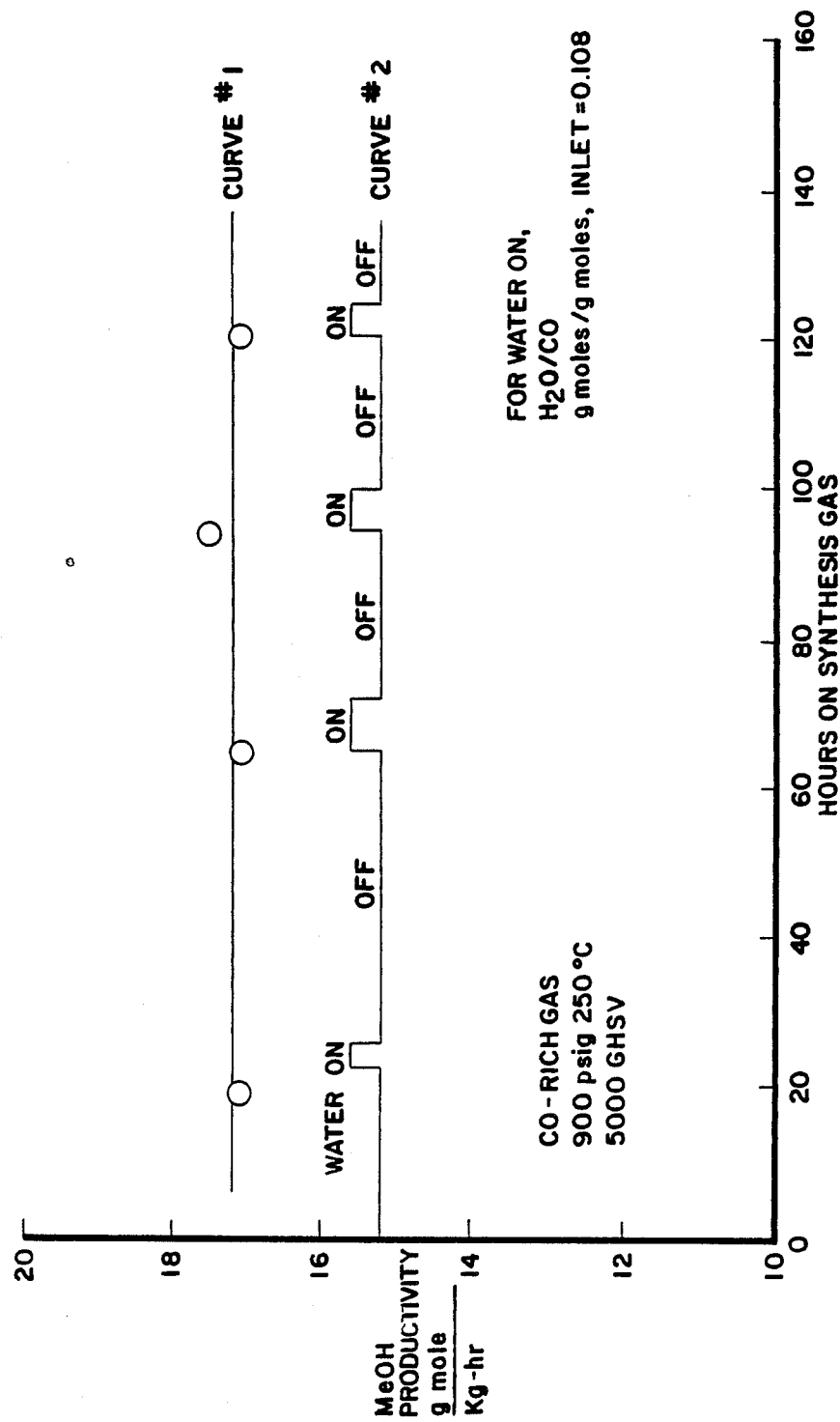
FIG. 4 is a plot of methanol productivity for a run with intermittent water addition.

FIG. 4 shows methanol productivity for a run with CO-rich syngas and intermittent water addition. Curve #1 shows the baseline methanol productivity trend when water is added as indicated by curve #2. The data points represent the methanol productivity during the periods without water addition; the productivity during periods with water addition always exceed the baseline curve #1. The important point here is that curve #1 is flat, rather than downward sloping, indicating that methanol productivity is not decreasing as was seen in FIG. 3. This is especially notable because the comparison is made during the hyperactivity period, when the rate of deactivation is most pronounced. Therefore, FIG. 4 indicates that the methanol productivity of the catalyst is preserved by the intermittent addition of water. Thus, the IGCC coproduction plant with water addition not only gets an additional degree of flexibility and a smaller reactor or incremental methanol production, but also a longer-lived catalyst.

In order to further demonstrate the efficacy of the present invention and to provide a description of several other process steps which can make the IGCC process more flexible, the following examples were simulated. In these examples a base case without water addition has been run for each of the process configurations.

EXAMPLES

EXAMPLE I

Figure 5:
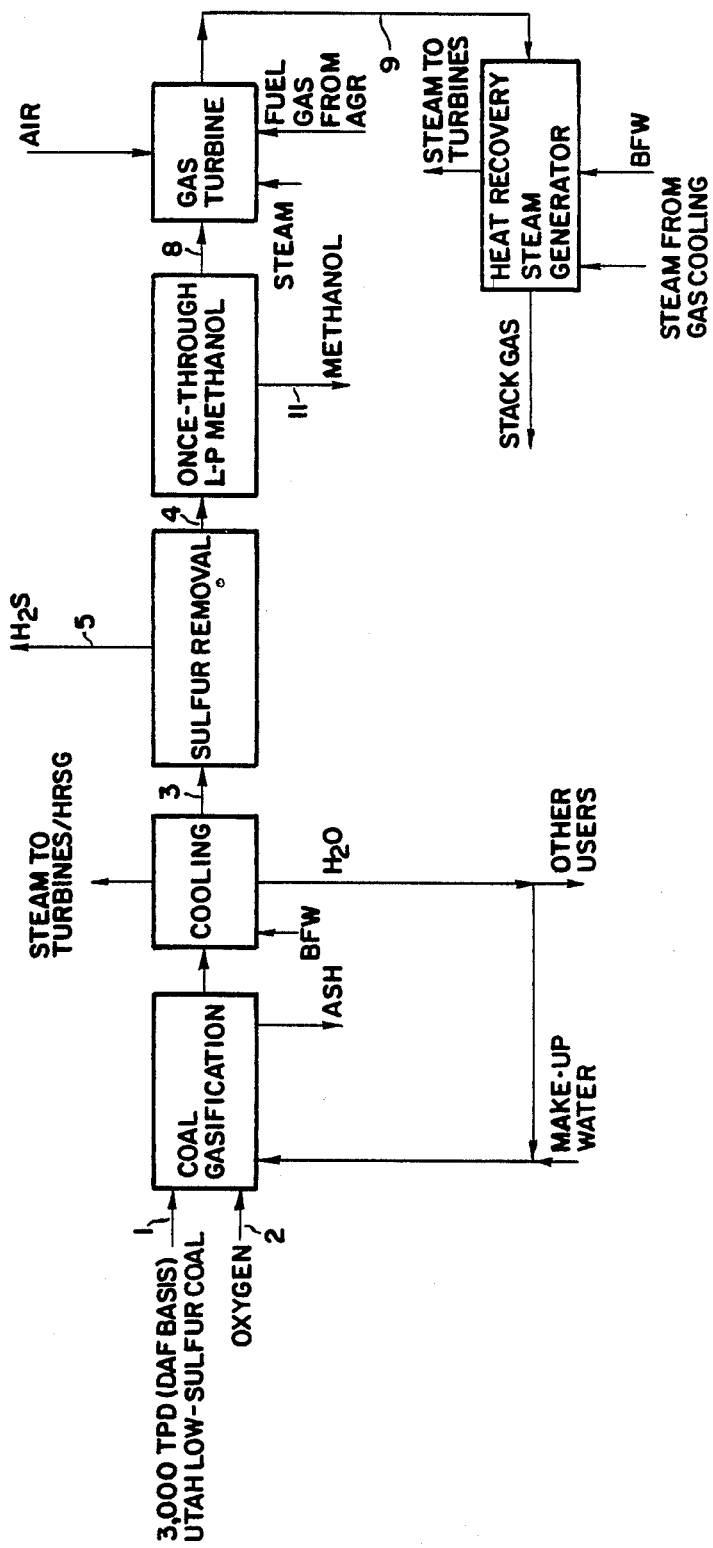
FIGS. 5 and 6 are block flow diagrams for a simple once-through liquid-phase methanol IGCC process.
Figure 6:
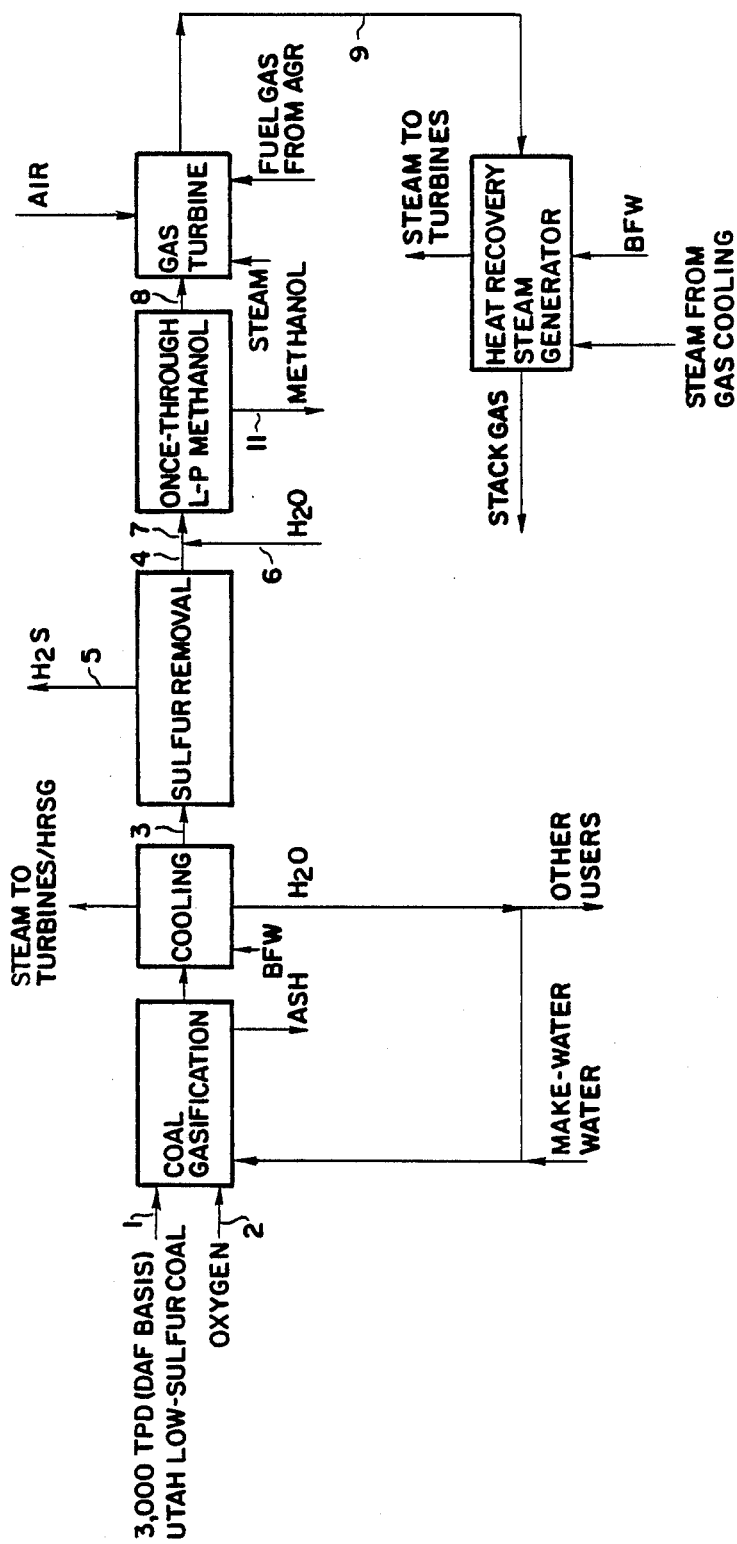

FIGS. 5 and 6 show block flow diagrams for a simple once-through liquid-phase methanol IGCC process. FIG. 5 shows the process without water addition and FIG. 6 with water addition. The corresponding material balances for 3,000 TPD of low sulfur coal for each figure are shown in Tables I and II, respectively.

TABLE I

IGCC LIQUID-PHASE METHANOL BASE CASE
FLOW RATES SHOWN ARE IN LBMOL/HR

| | STREAM NAME & NUMBER | | | | | | |
|---|---|---|---|---|---|---|---|
| COMPONENT | OXYGEN 2 | RAW GAS 3 | "CO-RICH" GAS 4 | ACID GAS 5 | FUEL GAS 8 | TURBINE EXHAUST 9 | CRUDE METHANOL 11 |
| $H_2$ | 0 | 8,648 | 8,645 | 3 | 4,638 | 0 | 0 |
| CO | 0 | 12,600 | 12,597 | 3 | 10,609 | 0 | 4 |
| $CO_2$ | 0 | 4,482 | 3,211 | 1,271 | 3,108 | 14,023 | 89 |
| $N_2(CH_4—Ar)$ | 173 | 409 | 247 | 162 | 247 | 122,921 | 0 |
| $O_2$ | 8,459 | 0 | 0 | 0 | 0 | 24,593 | 0 |
| $H_2S$ | 0 | 287 | 0 | 287 | 0 | 0 | 0 |
| COS | 0 | 19 | 0 | 19 | 0 | 0 | 0 |
| $H_2O$ | 0 | 0 | 0 | 0 | 0 | 12,952 | 14 |
| $CH_3OH$ | 0 | 0 | 0 | 0 | 169 | 0 | 1,828 |
| TOTAL (# MPH) | 8,632 | 26,445 | 24,700 | 1,745 | 18,771 | 174,489 | 1,935 |
| TOTAL (LB/HR) | 275,878 | 590,472 | 518,700 | 71,772 | 455,906 | 5,324,754 | 62,776 |

TABLE II

IGCC LIQUID-PHASE METHANOL WITH WATER ADDITION CASE
FLOW RATES SHOWN ARE IN LBMOL/HR

| | STREAM NAME & NUMBER | | | | | | | |
|---|---|---|---|---|---|---|---|---|
| COMPONENT | OXYGEN 2 | RAW GAS 3 | "CO-RICH" GAS 4 | ACID GAS 5 | WATER 6 | LPR INLET 7 | FUEL GAS 8 | TURBINE EXHAUST 9 | CRUDE METHANOL 11 |
| $H_2$ | 0 | 8,648 | 8,645 | 3 | 0 | 8,645 | 6,442 | 0 | 0 |
| CO | 0 | 12,600 | 12,597 | 3 | 0 | 12,597 | 8,349 | 0 | 3 |
| $CO_2$ | 0 | 4,482 | 3,211 | 1,271 | 0 | 3,211 | 5,160 | 13,818 | 147 |
| $N_2(CH_4—Ar)$ | 173 | 409 | 247 | 162 | 0 | 247 | 247 | 112,718 | 0 |
| $O_2$ | 8,459 | 0 | 0 | 0 | 0 | 0 | 0 | 22,103 | 0 |
| $H_2S$ | 0 | 287 | 0 | 287 | 0 | 0 | 0 | 0 | 0 |
| COS | 0 | 19 | 0 | 19 | 0 | 0 | 0 | 0 | 0 |
| $H_2O$ | 0 | 0 | 0 | 0 | 2,139 | 2,139 | 1 | 14,659 | 42 |
| $CH_3OH$ | 0 | 0 | 0 | 0 | 0 | 0 | 177 | 0 | 1,972 |
| TOTAL (# MPH) | 8,632 | 26,445 | 24,700 | 1,745 | 2,139 | 26,839 | 20,376 | 163,298 | 2,164 |

TABLE II-continued
IGCC LIQUID-PHASE METHANOL WITH WATER ADDITION CASE
FLOW RATES SHOWN ARE IN LBMOL/HR

| COMPONENT | OXYGEN 2 | RAW GAS 3 | "CO-RICH" GAS 4 | ACID GAS 5 | WATER 6 | LPR INLET 7 | FUEL GAS 8 | TURBINE EXHAUST 9 | CRUDE METHANOL 11 |
|---|---|---|---|---|---|---|---|---|---|
| TOTAL (LB/HR) | 275,878 | 590,472 | 518,700 | 71,772 | 38,502 | 557,202 | 486,787 | 4,960,690 | 70,406 |

EXAMPLE II

Figure 7:
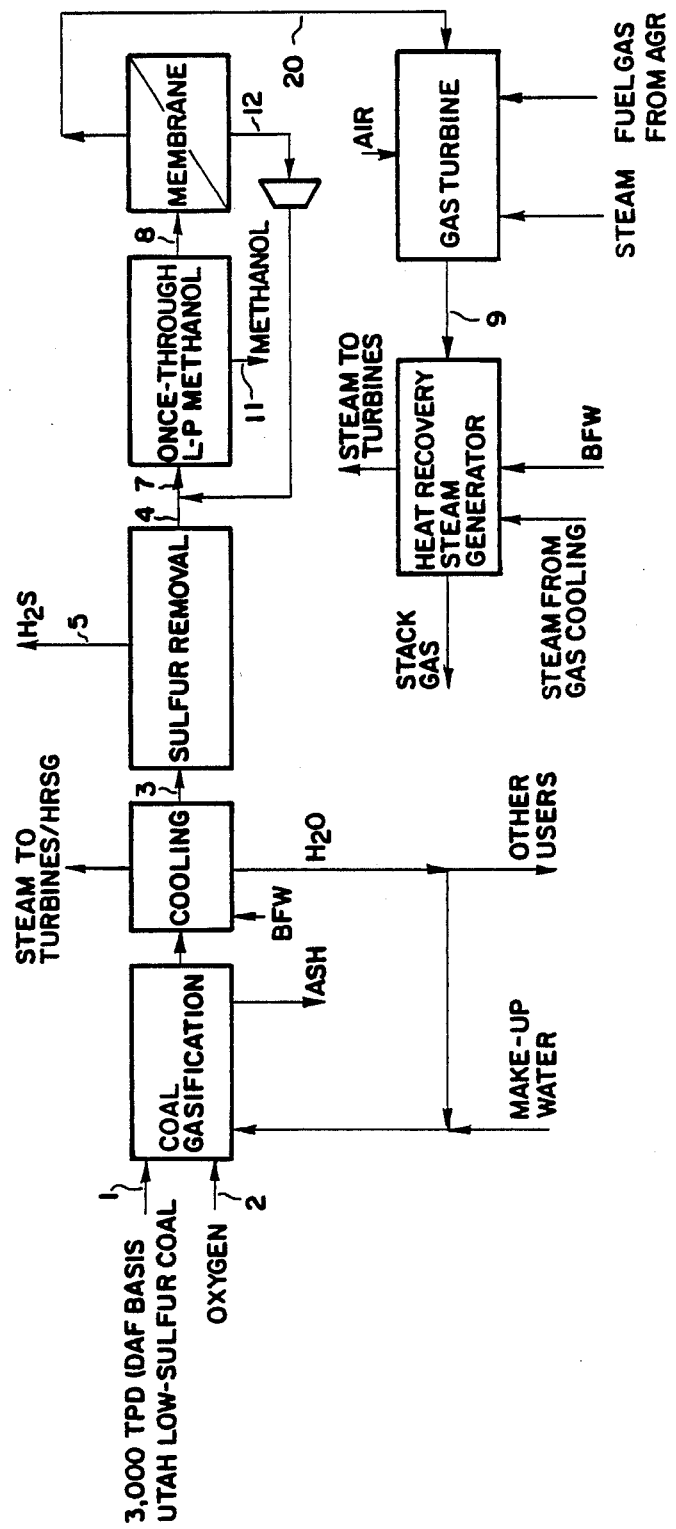
FIGS. 7 and 8 are block flow diagrams for a liquid-phase methanol IGCC process with a membrane recycle.
Figure 8:
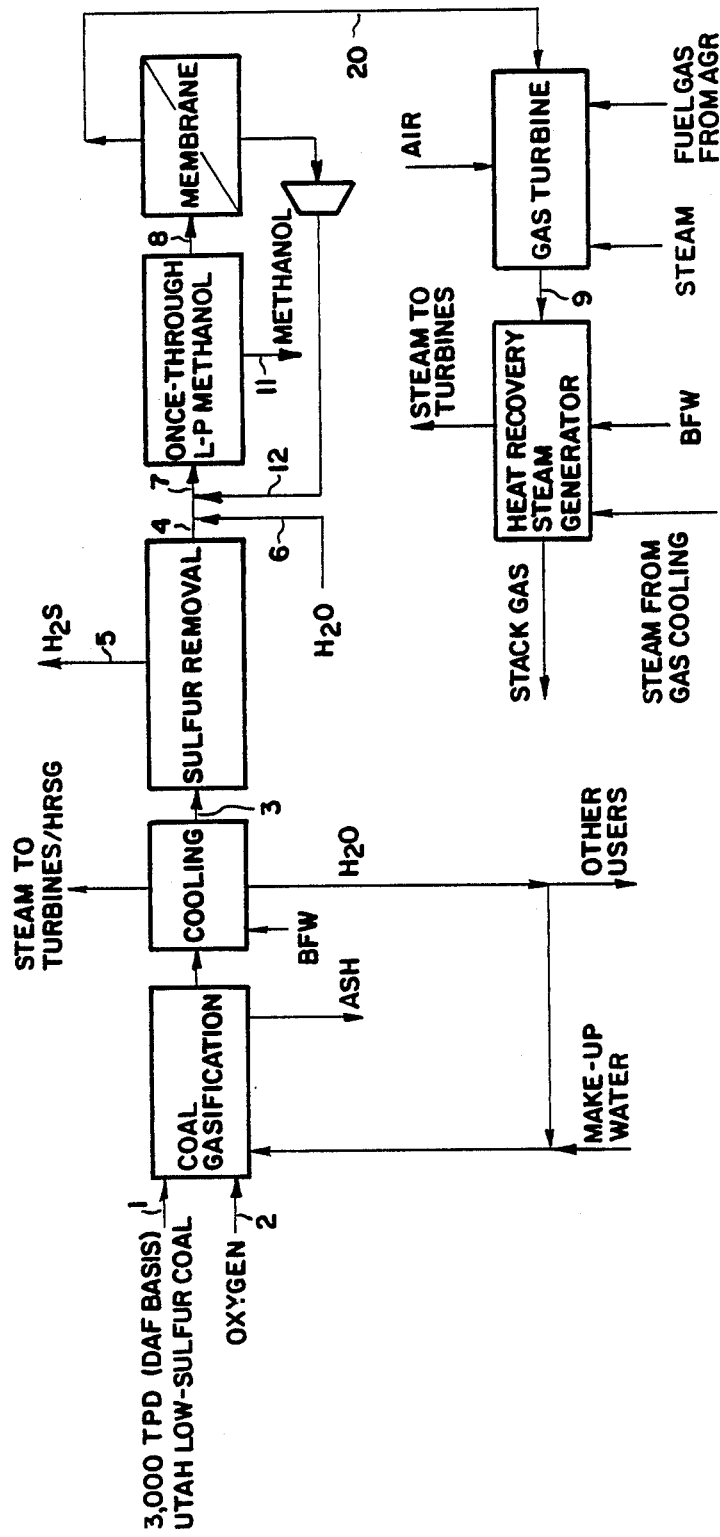

FIGS. 7 and 8 show block flow diagrams for a liquid-phase methanol IGCC process with a membrane recycle. FIG. 7 shows the process without water addition and FIG. 8 with water addition. The corresponding material balances for 3,000 TPD of low sulfur coal for each figure are shown in Tables III and IV, respectively.

It should be noted that the membrane material in this example is a commercially available cellulose acetate. Other membranes with higher $H_2/CO_2$ selectivities will permit even greater increases in methanol production.

TABLE III
IGCC LIQUID-PHASE METHANOL BASE CASE WITH MEMBRANE RECYCLE
FLOW RATES SHOWN ARE IN LBMOL/HR

| COMPONENT | OXYGEN 2 | RAW GAS 3 | "CO-RICH" GAS 4 | ACID GAS 5 | LPR INLET 7 | FUEL GAS 8 | MEMBRANE REJECT 20 |
|---|---|---|---|---|---|---|---|
| $H_2$ | 0 | 8,648 | 8,645 | 3 | 12,858 | 7,021 | 2,809 |
| CO | 0 | 12,600 | 12,597 | 3 | 13,159 | 10,280 | 9,718 |
| $CO_2$ | 0 | 4,482 | 3,211 | 1,271 | 5,267 | 5,023 | 2,963 |
| $N_2(CH_4—Ar)$ | 173 | 409 | 247 | 162 | 256 | 256 | 247 |
| $O_2$ | 8,459 | 0 | 0 | 0 | 0 | 0 | 0 |
| $H_2S$ | 0 | 287 | 0 | 287 | 0 | 0 | 0 |
| COS | 0 | 19 | 0 | 19 | 0 | 0 | 0 |
| $H_2O$ | 0 | 0 | 0 | 0 | 0 | 1 | 0 |
| $CH_3OH$ | 0 | 0 | 0 | 0 | 106 | 199 | 18 |
| TOTAL (# MPH) | 8,632 | 26,445 | 24,700 | 1,745 | 31,647 | 22,780 | 15,755 |
| TOTAL (LB/HR) | 275,878 | 590,472 | 518,700 | 71,772 | 637,029 | 536,960 | 416,095 |

| COMPONENT | TURBINE EXHAUST 9 | MEMBRANE PERMEATE 12 | CRUDE METHANOL 11 |
|---|---|---|---|
| $H_2$ | 0 | 4,213 | 0 |
| CO | 0 | 562 | 5 |
| $CO_2$ | 12,864 | 2,056 | 183 |
| $N_2(CH_4—Ar)$ | 97,782 | 9 | 0 |
| $O_2$ | 19,504 | 0 | 0 |
| $H_2S$ | 0 | 0 | 0 |
| COS | 0 | 0 | 0 |
| $H_2O$ | 10,542 | 0 | 38 |
| $CH_3OH$ | 0 | 106 | 2,804 |
| TOTAL (# MPH) | 140,692 | 6,947 | 3,030 |
| TOTAL (LB/HR) | 4,313,373 | 118,329 | 98,598 |

TABLE IV
IGCC LIQUID-PHASE METHANOL BASE CASE WITH MEMBRANE RECYCLE
AND WATER ADDITION
FLOW RATES SHOWN ARE IN LBMOL/HR

| COMPONENT | OXYGEN 2 | RAW GAS 3 | "CO-RICH" GAS 4 | ACID GAS 5 | WATER 6 | LPR INLET 7 | FUEL GAS 8 | MEMBRANE REJECT 20 |
|---|---|---|---|---|---|---|---|---|
| $H_2$ | 0 | 8,648 | 8,645 | 3 | 0 | 15,175 | 10,882 | 4,353 |
| CO | 0 | 12,600 | 12,597 | 3 | 0 | 13,012 | 7,858 | 7,444 |
| $CO_2$ | 0 | 4,482 | 3,211 | 1,271 | 0 | 6,536 | 8,220 | 4,893 |
| $N_2(CH_4—Ar)$ | 173 | 409 | 247 | 162 | 0 | 256 | 256 | 247 |
| $O_2$ | 8,459 | 0 | 0 | 0 | 0 | 0 | 0 | 0 |
| $H_2S$ | 0 | 287 | 0 | 287 | 0 | 0 | 0 | 0 |
| COS | 0 | 19 | 0 | 19 | 0 | 0 | 0 | 0 |
| $H_2O$ | 0 | 0 | 0 | 0 | 2,139 | 2,141 | 4 | 0 |
| $CH_3OH$ | 0 | 0 | 0 | 0 | 0 | 156 | 225 | 17 |
| TOTAL (# MPH) | 8,632 | 26,445 | 24,700 | 1,745 | 2,139 | 37,275 | 27,445 | 16,954 |
| TOTAL (LB/HR) | 275,878 | 590,472 | 518,700 | 71,772 | 38,502 | 733,445 | 618,412 | 440,380 |

| | STREAM NAME & NUMBER | | |
|---|---|---|---|
| | TURBINE EXHAUST | MEMBRANE PERMEATE | CRUDE METHANOL |

TABLE IV-continued
IGCC LIQUID-PHASE METHANOL BASE CASE WITH MEMBRANE RECYCLE AND WATER ADDITION
FLOW RATES SHOWN ARE IN LBMOL/HR

| COMPONENT | 9 | 12 | 11 |
|---|---|---|---|
| $H_2$ | 0 | 6,530 | 0 |
| CO | 0 | 415 | 3 |
| $CO_2$ | 12,533 | 3,325 | 268 |
| $N_2(CH_4-Ar)$ | 85,659 | 9 | 0 |
| $O_2$ | 16,656 | 0 | 0 |
| $H_2S$ | 0 | 0 | 0 |
| COS | 0 | 0 | 0 |
| $H_2O$ | 11,951 | 2 | 140 |
| $CH_3OH$ | 0 | 156 | 3,072 |
| TOTAL (# MPH) | 126,799 | 10,436 | 3,483 |
| TOTAL (LB/HR) | 3,869,329 | 176,243 | 112,688 |

EXAMPLE III

Figure 9:
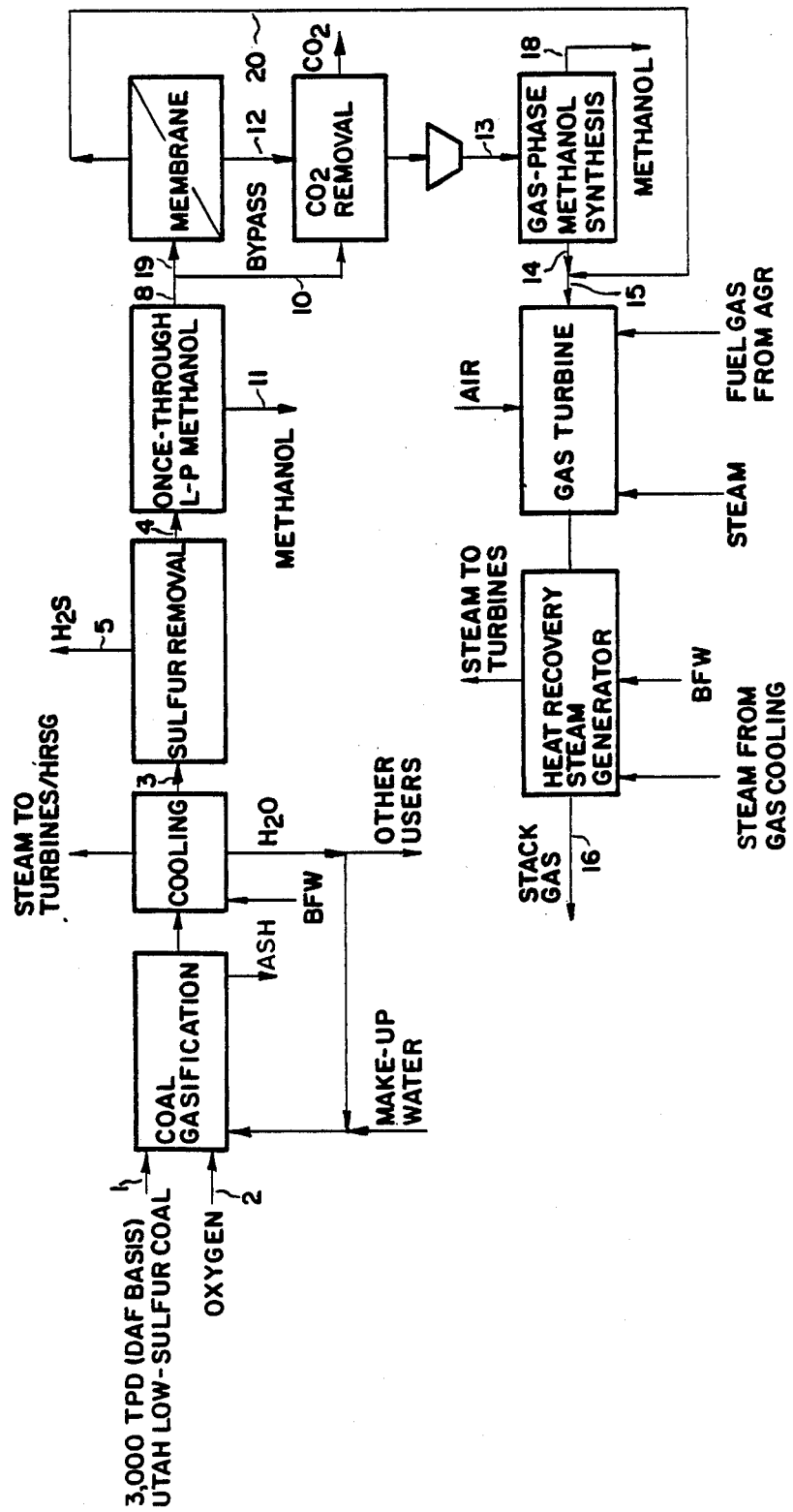
FIGS. 9 and 10 show block flow diagrams for a once-through liquid-phase methanol IGCC process with a membrane unit and a gas-phase methanol synthesis loop.
Figure 10:
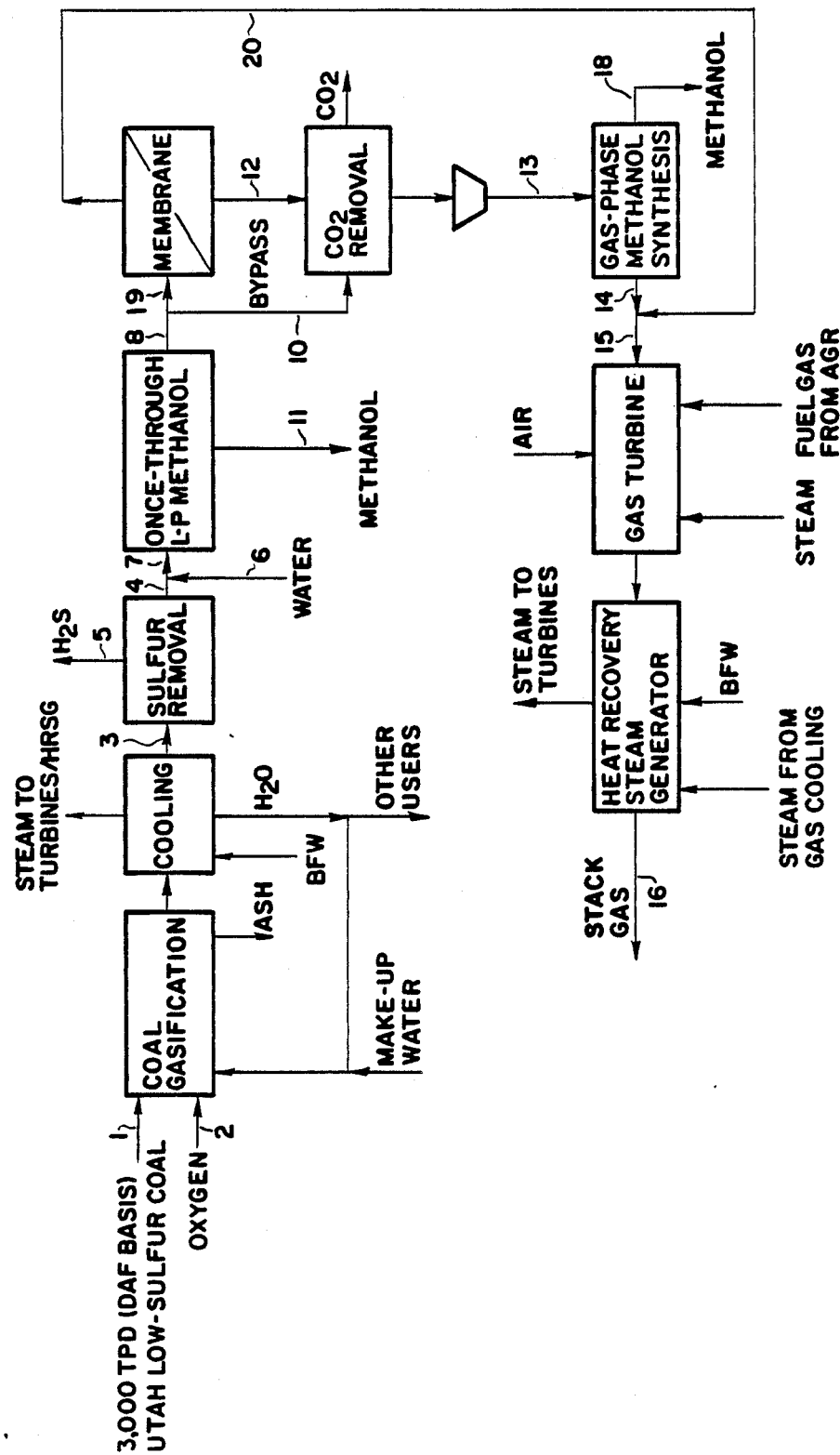

FIGS. 9 and 10 show block flow diagrams for a once-through liquid-phase methanol IGCC process with a membrane unit and a gas-phase methanol synthesis loop. FIG. 9 shows the process without water addition and FIG. 10 with water addition. The corresponding material balances for 3,000 TPD of low sulfur coal for each figure are shown in Tables V and VI, respectively.

In this example, the $H_2O/CO$ ratio is slightly higher than in Examples I and II to facilitate sufficient water-gas shift reaction to give a balanced syngas after membrane processing. As in Example II, the membrane material is cellulose acetate. Other membranes with higher $H_2/CO_2$ selectivity would provide additional benefits by reducing the load on the $CO_2$ removal unit and making more high pressure $CO_2$ available for power recovery in the gas turbine expander.

TABLE V
IGCC LIQUID-PHASE METHANOL BASE CASE WITH MEMBRANE RECYCLE AND GAS-PHASE METHANOL LOOP
FLOW RATES SHOWN ARE IN LBMOL/HR

| | STREAM NAME & NUMBER | | | | | | | |
|---|---|---|---|---|---|---|---|---|
| COMPONENT | OXYGEN 2 | RAW GAS 3 | "CO-RICH" GAS 4 | ACID GAS 5 | FLASH GAS 8 | MEMBRANE FEED 19 | MEMBRANE BYPASS 10 | MEMBRANE REJECT 20 |
| $H_2$ | 0 | 8,648 | 8,645 | 3 | 4,638 | 4,334 | 301 | 1,300 |
| CO | 0 | 12,600 | 12,597 | 3 | 10,609 | 9,910 | 689 | 9,161 |
| $CO_2$ | 0 | 4,482 | 3,211 | 1,271 | 3,108 | 2,898 | 202 | 1,421 |
| $N_2(CH_4-Ar)$ | 173 | 409 | 247 | 162 | 247 | 231 | 16 | 219 |
| $O_2$ | 8,459 | 0 | 0 | 0 | 0 | 0 | 0 | 0 |
| $H_2S$ | 0 | 287 | 0 | 287 | 0 | 0 | 0 | 0 |
| COS | 0 | 19 | 0 | 19 | 0 | 0 | 0* | 0 |
| $H_2O$ | 0 | 0 | 0 | 0 | 0 | 0 | 0 | 0 |
| $CH_3OH$ | 0 | 0 | 0 | 0 | 169 | 157 | 11 | 9 |
| TOTAL (# MPH) | 8,632 | 26,445 | 24,700 | 1,745 | 18,771 | 17,530 | 1,219 | 12,110 |
| TOTAL (LB/HR) | 275,878 | 590,472 | 518,700 | 71,772 | 455,906 | 425,591 | 29,592 | 328,475 |

| | STREAM NAME & NUMBER | | | | | | | |
|---|---|---|---|---|---|---|---|---|
| COMPONENT | MEMBRANE PERMEATE 12 | GAS-LOOP FEED 13 | FLASH GAS 14 | G.T. FEED 15 | STACK GAS 16 | LPR CRUDE 11 | GAS-LOOP CRUDE 18 | TOTAL CRUDE MEOH |
| $H_2$ | 3,034 | 3,335 | 323 | 1,623 | 0 | 0 | 7 | 7 |
| CO | 749 | 1,438 | 67 | 9,227 | 0 | 4 | 5 | 10 |
| $CO_2$ | 1,476 | 101 | 4 | 1,425 | 10,805 | 89 | 7 | 95 |
| $N_2(CH_4-Ar)$ | 11 | 28 | 27 | 246 | 85,230 | 0 | 0 | 0 |
| $O_2$ | 0 | 0 | 0 | 0 | 17,028 | 0 | 0 | 0 |
| $H_2S$ | 0 | 0 | 0 | 0 | 0 | 0 | 0 | 0 |
| COS | 0 | 0 | 0 | 0 | 0 | 0 | 0 | 0 |
| $H_2O$ | 0 | 0 | 0 | 0 | 9,198 | 14 | 91 | 105 |
| $CH_3OH$ | 148 | 159 | 2 | 11 | 0 | 1,828 | 1,615 | 3,443 |
| TOTAL (# MPH) | 5,419 | 5,062 | 422 | 12,532 | 122,261 | 1,935 | 1,725 | 3,660 |
| TOTAL (LB/HR) | 97,094 | 57,319 | 3,544 | 332,018 | 3,742,780 | 62,776 | 53,771 | 116,538 |

TABLE VI
IGCC LIQUID-PHASE METHANOL BASE CASE WITH MEMBRANE RECYCLE, GAS-PHASE METHANOL LOOP, AND WITH WATER ADDITION
FLOW RATES SHOWN ARE IN LBMOL/HR

| | STREAM NAME & NUMBER | | | | | | | |
|---|---|---|---|---|---|---|---|---|
| COMPONENT | OXYGEN 2 | RAW GAS 3 | "CO-RICH" GAS 4 | ACID GAS 5 | WATER 6 | LPR INLET 7 | FLASH GAS 8 | MEMBRANE FEED 19 |
| $H_2$ | 0 | 8,648 | 8,645 | 3 | 0 | 8,645 | 6,836 | 5,344 |
| CO | 0 | 12,600 | 12,597 | 3 | 0 | 12,597 | 7,755 | 6,061 |
| $CO_2$ | 0 | 4,482 | 3,211 | 1,271 | 0 | 3,211 | 5,641 | 4,409 |

TABLE VI-continued
IGCC LIQUID-PHASE METHANOL BASE CASE WITH MEMBRANE RECYCLE, GAS-PHASE METHANOL LOOP, AND WITH WATER ADDITION
FLOW RATES SHOWN ARE IN LBMOL/HR

| | | | | | | | | |
|---|---|---|---|---|---|---|---|---|
| $N_2(CH_4-Ar)$ | 173 | 409 | 247 | 162 | 0 | 247 | 247 | 193 |
| $O_2$ | 8,459 | 0 | 0 | 0 | 0 | 0 | 0 | 0 |
| $H_2S$ | 0 | 287 | 0 | 287 | 0 | 0 | 0 | 0 |
| COS | 0 | 19 | 0 | 19 | 0 | 0 | 0 | 0 |
| $H_2O$ | 0 | 0 | 0 | 0 | 2,674 | 2,674 | 2 | 1 |
| $CH_3OH$ | 0 | 0 | 0 | 0 | 0 | 0 | 177 | 139 |
| TOTAL (# MPH) | 8,632 | 26,445 | 24,700 | 1,745 | 2,674 | 27,374 | 20,658 | 16,147 |
| TOTAL (LB/HR) | 275,878 | 590,472 | 518,700 | 71,772 | 48,132 | 566,832 | 492,115 | 384,657 |

STREAM NAME & NUMBER

| COMPONENT | MEMBRANE BYPASS 10 | MEMBRANE REJECT 20 | MEMBRANE PERMEATE 12 | GAS-LOOP FEED 13 | FLASH GAS 14 | G.T. FEED 15 |
|---|---|---|---|---|---|---|
| $H_2$ | 1,493 | 2,137 | 3,206 | 4,699 | 468 | 2,605 |
| CO | 1,693 | 5,734 | 327 | 2,021 | 94 | 5,828 |
| $CO_2$ | 1,232 | 2,609 | 1,800 | 142 | 5 | 2,614 |
| $N_2(CH_4-Ar)$ | 54 | 186 | 7 | 61 | 60 | 246 |
| $O_2$ | 0 | 0 | 0 | 0 | 0 | 0 |
| $H_2S$ | 0 | 0 | 0 | 0 | 0 | 0 |
| COS | 0 | 0 | 0 | 0 | 0 | 0 |
| $H_2O$ | 0 | 0 | 1 | 2 | 0 | 0 |
| $CH_3OH$ | 39 | 12 | 127 | 166 | 3 | 15 |
| TOTAL (# MPH) | 4,511 | 10,679 | 5,468 | 7,089 | 630 | 11,308 |
| TOTAL (LB/HR) | 107,458 | 285,594 | 99,062 | 79,359 | 5,674 | 291,268 |

STREAM NAME & NUMBER

| COMPONENT | STACK GAS 16 | LPR (RUDE) 11 | GAS-LOOP CRUDE 18 | TOTAL CRUDE MEOH |
|---|---|---|---|---|
| $H_2$ | 0 | 0 | 9 | 9 |
| CO | 0 | 3 | 7 | 9 |
| $CO_2$ | 8,605 | 163 | 9 | 172 |
| $N_2(CH_4-Ar)$ | 58,993 | 0 | 1 | 1 |
| $O_2$ | 11,274 | 0 | 0 | 0 |
| $H_2S$ | 0 | 0 | 0 | 0 |
| COS | 0 | 0 | 0 | 0 |
| $H_2O$ | 9,893 | 54 | 129 | 183 |
| $CH_3OH$ | 0 | 2,034 | 2,210 | 4,244 |
| TOTAL (# MPH) | 88,764 | 2,254 | 2,364 | 4,617 |
| TOTAL (LB/HR) | 2,687,237 | 73,289 | 73,652 | 146,941 |

As can be seen from the Examples, the present invention includes several other process variations which add even more flexibility to the IGCC coproduction flowsheet. FIG. 8 shows a proposed block flow diagram for a plant which incorporates a membrane loop into the effluent fuel gas stream to recover hydrogen for recycle to the liquid-phase reactor. The recycled hydrogen increase the feed $H_2$/CO ratio to the reactor, which increases methanol production. The membrane can be used in conjunction with water addition to the liquid-phase methanol reactor, or without water addition. Mass and energy balances indicate that daily methanol production can be increased by 53% by using the membrane alone, and by an additional 15% by using both the membrane and water addition.

FIG. 10 shows a proposed block flow diagram for an IGCC coproduction scheme which incorporates water addition, membrane $H_2$ recovery, and a gas-phase methanol loop. Here, a portion of the fuel gas bypasses the membrane so that, after $CO_2$ removal from this stream and the membrane effluent, the combined stream is balanced. This balanced gas is fed to a conventional gas-phase methanol reactor, after which the methanol is recovered and the unreacted purge gas is sent to the gas turbine.

Table VII itemizes the relative methanol production which can be achieved in these various IGCC coproduct configurations. As seen, there are a total of 6 options available. Clearly there is significant flexibility available through practicing this invention.

TABLE VII
RELATIVE METHANOL PRODUCTION FOR IGCC COPRODUCT PLANT VARIATIONS USING COMBINED SHIFT/SYNTHESIS

| Option | | Methanol Production Compared to Option #1 |
|---|---|---|
| 1. | Once Through Liquid-Phase Methanol | 100% |
| 2. | With Water Addition | 108% |
| 3. | With Membrane Recycle | 153% |
| 4. | With Membrane Recycle and Water Addition | 168% |
| 5. | With Membrane Recycle Gas-Phase MeOH Loop | 188% |
| 6. | With Membrane Recycle Gas-Phase MeOH Loop and Water Addition | 232% |

The present invention has been described with reference to a specific embodiment thereof. This embodiment should not be considered a limitation on the scope of the present invention; the scope of which should be ascertained by the following claims.

We claim:

1. In an integrated gasification combined cycle (IGCC) electric power plant process wherein the IGCC process converts hydrocarbon fuels in a gasifier producing a carbon monoxide-rich synthesis gas, which in turn is combusted in a gas turbine to produce power; wherein the IGCC process also includes a provision for production of methanol from the carbon monoxide-rich synthesis gas prior to combustion; and wherein methanol is produced by reacting at least a portion of the carbon monoxide-rich synthesis gas in the presence of a methanol synthesis catalyst; the improvement for increasing methanol productivity which comprises combining water/gas shift and methanol synthesis reactions in a single step by reacting the portion of the carbon monoxide-rich synthesis gas with water in the presence of a catalyst in a liquid-phase reactor thereby producing both a crude methanol product and a reduced carbon monoxide content and increased hydrogen and carbon dioxide content synthesis gas for combustion; and processing a first portion of the reduced carbon monoxide content and increased hydrogen and carbon dioxide content synthesis gas to separate the reduced carbon monoxide content and increased hydrogen and carbon dioxide content synthesis gas into a hydrogen-rich component and a carbon monoxide-rich component, both components comprising hydrogen, carbon dioxide and carbon monoxide, combining the hydrogen-rich component and a second portion of the reduced carbon monoxide content and increased hydrogen and carbon dioxide content synthesis gas to form a gas-phase methanol reactor feed stream, reacting the gas-phase methanol reactor feed stream in a gas-phase reactor to produce methanol, and combining the unconverted effluent from the gas-phase methanol reactor with the carbon monoxide-rich component to form a gas turbine combustion feed.

2. The process of claim 1 which further comprises removing at least a portion of the carbon dioxide from the gas-phase methanol reactor feed stream prior to reacting the gas-phase methanol reactor feed stream in the gas-phase reactor to produce methanol.

3. The process of claim 2 wherein separation of the reduced carbon monoxide content and increased hydrogen and carbon dioxide content synthesis gas is accomplished in a membrane unit.

* * * * *